United States Patent [19]

Hayama et al.

[11] 4,358,567

[45] Nov. 9, 1982

[54] RESINS FOR HAIRDRESSINGS

[75] Inventors: Kazuhide Hayama; Kanji Narazaki, both of Yokkaichi, Japan

[73] Assignee: Mitsubishi Petrochemical Company Limited, Japan

[21] Appl. No.: 117,289

[22] Filed: Jan. 31, 1980

[30] Foreign Application Priority Data

Feb. 6, 1979 [JP] Japan .................................. 54-12380
Dec. 27, 1979 [JP] Japan ................................ 54-173670

[51] Int. Cl.$^3$ ................................................ C08F 8/18
[52] U.S. Cl. ............................... 525/359.4; 525/293; 525/296
[58] Field of Search .................. 525/359, 293, 359.4, 525/296

[56] References Cited

U.S. PATENT DOCUMENTS 3,934,595 1/1976 Madrange et al. ................... 525/359

OTHER PUBLICATIONS

IARC Monographs, vol. 20, International Agency for Research on Cancer, World Health Organization, "IARC Monographs on the Evaluation of the Carcinogenic Risk of Chemicals to Humans".
Shell International Research Maatschappij B.V. 1980, "Principles for the Safe Handling of Mutagens, Carcinogens and Teratogens".
Kirk Othmer, Encyclopedia of Chemical Tech., vol. 8, pp. 415-416.

*Primary Examiner*—William F. Hamrock
*Attorney, Agent, or Firm*—Robert E. Burns; Emmanuel J. Lobato; Bruce L. Adams

[57] ABSTRACT

A resin for hairdressing is obtained by: copolymerizing in a hydrophilic solvent a monomer (1), which is specific derivative of acrylic or methacrylic acid, and a monomer (3), which is a specific (meth)acrylic acid ester, and, optionally in addition, any of a monomer (2), which is another specific (meth)acrylic acid ester, and monomer (4), which is a hydrophilic ethylenically unsaturated monomer, and a monomer (5), which is an ethylenically unsaturated monomer other than the monomers (1) through (4); causing the copolymer thus formed to react in the state of a solution in a hydrophilic solvent with sodium or potassium haloacetate; removing any precipitate formed as by-product; and, if necessary, subjecting the copolymer solution thus obtained to an ion-exchange resin treatment thereby to remove ionic impurities.

14 Claims, No Drawings

RESINS FOR HAIRDRESSINGS

BACKGROUND OF THE INVENTION

This invention relates generally to resins for hairdressings and more particularly to water-soluble ampho-ionic resins which exhibit excellent effectiveness as hairdressings.

The resins for hairdressings according to this invention are particularly suitable for use in the form of aerosols.

The practice of fixing or setting hair on human heads with resins thereby to impart a desired headdress shape thereto is known. For facility in removal by shampooing, hairdressing resins should be water soluble.

As such hairdressing resins, nonionic, anionic, and cationic resins have heretofore been used. Such resins known in the prior art, however, cannot be said to be fully satisfactory in all cases.

More specifically, polyvinyl methyl ether and polyvinyl pyrrolidone are well known examples of nonionic resins. Polyvinyl pyrrolidone resins are easily affected by humidity conditions, and films thereof prior to absorption of moisture are hard and are readily subject to a flaking phenomenon. On the other hand, these resins become extremely soft under high-temperature high-humidity condition and give rise to a blocking phenomenon. As a consequence, when these resins are applied under these conditions to the head, the hair filaments stick to each other, whereby combing or brushing becomes difficult or may become impossible. These effects due to humidity are even more pronounced in the case of polyvinyl methyl ether resins.

As anionic resins, copolymers resins having a vinyl carboxylic acid such as, for example, acrylic acid or methacrylic acid, as an ionic radical are known and are at present the most widely used resins for hairdressing. These anionic resins are not readily affected by humidity and exhibit better properties than nonionic resins but, because they are anionic, have weak affinity with respect to hair. On one hand, films of these resins must be hard for increased hairdressing effectiveness, but this increases the possibility of flaking phenomenon. Furthermore, because these resins are anionic, the addition thereto of cationic substances is limited, and there is the possibility of caking phenomenon due to agents such as a rinsing agent at the time of shampooing.

Cationic resins have greater affinity than nonionic and anionic resins with respect to hair but, similarly as in the case of nonionic resins, are readily affected by humidity. Furthermore, because these resins are cationic, there is the risk of their being toxic or epispastic. The addition to these resins of anionic substances is also limited, and there is the problem of caking phenomenon due to the shampoo (anionic) during shampooing.

That excellent resin compositions for hairdressing (for fixing or setting hair in place) are obtained by using resins having an ampho-ionic property has previously been disclosed by us in Japanese Patent Laid Open Publication No. 9732/1976. In this case, however, during the ampho-ionization of the copolymer, precipitation occurs in some instances at the time of modification when a sodium salt or a potassium salt of halo-acetic acid is used, and, because of the resulting precipitate, the properties of the film are not always good. Furthermore, in the case where the preparation is used in the form of an aerosol, the container vessel tends to be readily corroded.

SUMMARY OF THE INVENTION

As a result of our various studies directed toward solutions of the above described problems, we have found that an excellent resin for hairdressing (hair fixing) can be obtained by removing the substances which precipitate at the time when, in the above mentioned use of resins having ampho-ionic property, modification is carried out with a sodium salt or potassium salt of haloacetic acid. This discovery forms a basis of this invention.

More specifically, according to this invention in one aspect thereof, there are provided resins for hairdressings, each of which is characterized in that it is obtained by a process which comprises:

copolymerizing, in a hydrophilic solvent, monomers of a monomer composition comprising:
25 to 45 percent by weight of a first monomer (1) represented by the formula

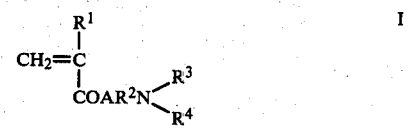

0 to 50 percent by weight of a second monomer (2) represented by the formula

5 to 65 percent by weight of a third monomer (3) represented by the formula

0 to 20 percent by weight of a fourth monomer (4) which is a hydrophilic ethylenically unsaturated monomer, and 0 to 20 percent by weight of a fifth monomer (5) which is an ethylenically unsaturated monomer other than the monomer (1) through (4), the total content of the monomer (1) unit and the monomer (4) unit being 35 percent by weight at the least, in which formulas:

$R^1$ is a hydrogen atom or a methyl radical; $R^2$ is an alkylene radical having 1 to 4 carbon atoms; each of $R^3$ and $R^4$ is a hydrogen atom or an alkyl radical having 1 to 4 carbon atoms; $R^5$ is an alkyl or alkenyl radical having 1 to 3 carbon atoms; $R^6$ is an alkyl or alkenyl radical having 4 to 24 carbon atoms or a cycloalkyl radical having 4 to 24 carbon atoms; and A is oxygen (O) or NH;

causing the copolymer thus formed to react in the state of a solution in a hydrophilic solvent with sodium or potassium haloacetate;

removing any precipitate formed as by-product; and, if necessary, subjecting the copolymer solution thus obtained to an ion-exchange resin treatment thereby to remove ionic impurities.

According to this invention in another aspect thereof, there is provided the process ad described above of producing the resins for hairdressing.

According to this invention, there are provided resins having properties that are highly suitable for use as hairdressings particularly in the form of aerosols. More specifically, each resin of this invention is soluble in water or in a hydrophilic organic solvent. Furthermore, solutions obtained by using these solvents exhibit good solubility with respect to propellants in general. Further, each of the resins of this invention can be easily washed and removed by shampooing.

In addition to the above enumerated general features of hairdressings preparations, the hairdressings resins according to this invention have the following desirable features:

(1) Each resin has a strong affinity with respect to hair, and, in spite of the suppleness or flexibility of a film thereof, it has excellent hairdressing effectiveness and does not cause flaking.

(2) The resin applied to the hair does not cause a blocking sensation even at a high temperature and high humidity.

(3) In spite of the moisture absorbing characteristic of a film of the resin, the film has excellent hairdressing effectiveness at a high temperature and high humidity. Furthermore, because of this moisture absorbing characteristic, the resin exhibits an antistatic effectiveness with respect to hair, whereby dust, grime, etc., do not readily adhere to the dressed hair.

(4) Ionic shocks do not occur no matter what charged substance is added to the resin, and caking is not caused by the use of an anionic or cationic surfactant at the time of shampooing.

(5) The resin has excellent compatibility with additives, particularly with anionic and cationic surfactants.

(6) The resin has extremely low degrees of toxicity and epispasticity.

(7) When applied as hairdressing, the resin has a good tactile feel and imparts an extremely natural sensation.

(8) When the resin is packaged in the form of an aerosol, the aerosol container is not corroded.

DETAILED DESCRIPTION

Throughout this disclosure, all quantities (including concentrations) expressed in percent are by weight.

1. Monomers

A resin according to this invention is prepared by ampho-ionizing a copolymer of two indispensable species of monomers (monomers (1) and (3)) and any of three species of monomers (monomers (2), (4), and (5)). These monomers can be used jointly within their respective groups.

1-1. Monomer (1)

The monomer (1) is a derivative as represented by the formula (I) set forth hereinbefore of acrylic acid or methacrylic acid (hereinafter referred to as (meth)acrylic acid). In the formula, the substituents have their respective meanings stated hereinbefore, but, in general, it is preferable that $R^1$ be methyl, $R^2$ be $C_2$ or $C_3$, each of $R^3$ and $R^4$ by $C_1$ or $C_2$, and A be 0.

Specific examples of the monomer (1) are dimethylaminoethyl (meth)acrylate, diethylaminoethyl (meth)acrylate, dimethylaminopropyl (meth)acrylate, dimethylaminoethyl (meth)acrylamide, and diethylaminopropyl (meth)acrylamide.

The quantity in which the monomer (1) is used is 25 to 45 percent, preferably 30 to 40 percent, relative to the total quantity of monomers. We have found that when this quantity is less than 25 percent, the resulting film of the final ampho-ionized copolymer does not readily dissolve in water, and it is difficult to remove by washing at the time of shampooing. In addition, the affinity of this copolymer with respect to hair, which is a feature arising from its being ampho-ionic, is reduced, as a result of which problems such as the occurrence of flaking, lowering of the antistatic effect, and deterioration of the natural feel as a hairdressing arise. On the other hand, when the quantity of the monomer (1) exceeds 45 percent, the film of the resulting copolymer tends to impart a blocking sensation, and the setting strength deteriorates. Furthermore, when this copolymer is used in the form of an aerosol, the solubility of the propellant therein decreases.

While, the quantities of the monomers (1) through (5) in this invention relate to the monomer composition based on the total quantity of the monomers used, when the rate of polymerization of the copolymerization is substantially 100 percent (which is ordinarily the case), this means that this composition is substantially the same as the monomer unit composition of the copolymer prior to ampho-ionization.

1-2. Monomer (2)

The monomer (2) is a (meth)acrylic acid ester represented by the formula (II) given hereinbefore, in which it is preferable, in general, that $R^1$ be methyl and $R^5$ be alkyl.

Specific examples of the monomer (2) are methyl (meth)acrylate, ethyl (meth)acrylate, propyl (meth)acrylates, butyl (meth)acrylates, and allyl (meth)acrylate.

The quantity in which the monomer (2) is used is 0 to 50 percent, preferably 5 to 40 percent, relative to the total quantity of the monomers used. We have found that when this quantity of the monomer (2) exceeds 50 percent, the suppleness or flexibility of the film of the copolymer becomes poor, and, at the same time, the solubility of a propellant in the copolymer decreases.

1-3. Monomer (3)

The monomer (3) is a (meth)acrylic acid ester represented by the aforegiven formula (III). In comparison with the monomer (2), the chain length of the alcohol portion is longer. It is preferable, in general, that $R^1$ be methyl and $R^6$ be $C_4$ through $C_{18}$.

Specific examples of the monomer (3) are 2-ethylhexyl (meth)acrylate, stearyl (meth)acrylate, lauryl (meth)acrylate, isobutyl (meth)acrylate, cyclohexyl (meth)acrylate, and oleyl (meth)acrylate.

The monomer (3) is used in a quantity of 5 to 65 percent, preferably 10 to 50 percent with respect to the total quantity of monomers. We have found that when this quantity of the monomer (3) is less than 5 percent, the humidity resistance (i.e., setting strength under high humidity) of the resulting copolymer decreases, and the flexibility of a film thereof becomes poor. At the same time, the solubility of a propellant therein is reduced. On the other hand, when this quantity exceeds 65 percent, the film of the resulting copolymer imparts a blocking sensation, and the smoothness and transparency of the film become poor. Furthermore, the copolymer is not easily dissolved in water, and it becomes difficult to remove by washing during shampooing.

1-4. Monomer (4)

The monomer (4), which is hydrophilic, ethylenically unsaturated, can further be caused to copolymerize in order to improve the water solubility of the final ampho-ionized copolymer thereby to facilitate the removal thereof by washing at the time of shampooing. The descriptive phrase "the monomer (4), which is hydrophilic, ethylenically unsaturated" used herein designates a monomer whose solubility in water is at least 10 gram/100 gram of water at 25° C. Furthermore, in general, it is preferable that is monomer be nonionic.

Specific examples of this monomer (4) are N-vinyl pyrrolidone, acrylamide, hydroxyethyl or propyl (meth)acrylate, and polyethylene or propyleneglycol mono(meth)acrylate.

The monomer (4) is used in a quantity of 0 to 20 percent, preferably 0 to 15 percent, with respect to the total quantity of the monomers. At the same time, the sum of the quantity of this monomer (4) and that of the monomer (1) is 35 percent or more, preferably 35 to 50 percent, of the total monomer quantity. We have found that when the quantity of the monomer (4) itself exceeds 20 percent, the hydrophilic property of the resulting copolymer is improved, but its setting strength under high humidity decreases, while a film thereof imparts a blocking sensation. On the other hand, when the above mentioned sum of the quantities of the monomers (4) and (1) is less than 35 percent, the water solubility of the ampho-ionic copolymer is insufficient.

1-5. Monomer (5)

In order to impart a suitable flexibility and an appropriate hardness to a film of the final ampho-ionic copolymer thereby to vary the feel thereof, an ethylenically unsaturated monomer other than the above described monomers (1) through (4) can be caused to copolymerize therewith.

Specific examples of such a monomer (5) are acrylonitrile, styrene, chlorostyrene, vinyltoluene, vinyl acetate, polypropylene glycol mono(meth)acrylate, vinyltrichlorosilane, and methacryloxypropyl trimethoxy silane.

The quantity in which this monomer (5) is used is 0 to 20 percent, preferably 0 to 10 percent, relative to the total quantity of the monomers.

2. Polymerization

The above described three to five kinds of monomers are copolymerized in a hydrophilic solvent. The term "hydrophilic solvent" is herein used to designate an organic solvent whose solubility in water is at least 10 gram/100 gram of water at 25° C.

Specific examples of hydrophilic organic solvents suitable for use in the practice of this invention are: aliphatic monohydric to tetrahydric alcohols having 1 to 4 carbon atoms, particularly monohydric alcohols such as methanol, ethanol, and isopropanol and dihydric alcohols such as ethylene glycol; ethyl Cellosolve; buty Cellosolve; dioxane; methyl acetate; and dimethylformamide.

The "hydrophilic solvent" may be in a water-containing state. The order of water content, in view of the solvent for the polymerization, may be any within a range wherein the entire quantity of the monomers will dissolve to a specific concentration. (The limitation of the order of water content in view of the function of the solvent as a solvent for ampho-ionization reaction will be considered hereinafter). A specific example of a water-containing hydrophilic solvent is 95-percent ethanol.

The polymerization is carried out by an ordinary method of solution polymerization such as, for example, the method which comprises dissolving each monomer in the above described solvent, adding thereto a polymerization initiator, and heating and agitating the reaction materials in a stream of nitrogen. For the polymerization initiator a peroxide such as benzoyl peroxide or lauroyl peroxide or an azo compound such as azobisisobutyronitrile is preferred. While the ordinary procedure is to cause all of the selected monomers in their respective total quantities to be present in the polymerization from the start thereof, it is possible to add the monomers in a divisional manner with respect to their kinds and(or) quantities. The quantity of the solvent used is preferably such that the concentration of the copolymer solution formed will be of the order of 30 to 65 percent.

3. Ampho-ionization

The copolymer of three to five components obtained in this manner is caused to react with sodium or potassium haloacetate. In this case, this "reaction" is understood to be an ampho-ionization which comprises the introduction of an acetic acid radical into the amino radical of the monomer (1). As a result of this reaction, a sodium or potassium halide originating from the sodium or potassium haloacetate used is produced as a by-product.

The ampho-ionization reaction is carried out with respect to the solution of the copolymer in the hydrophilic solvent obtained in the above described manner. The definition of the hydrophilic solvent in this case is the same as that of the above described solvent for polymerization. However, in view of the removal of inorganic salts produced as by-product of the ampho-ionization reaction as a precipitate, which is one feature of this invention, the solvent for the ampho-ionization reaction should be one in which the solubilities of the by-product inorganic salts are sufficiently low. Accordingly, it is preferable that the order of water content of this hydrophilic solvent be amply low. Provided that consideration is given to this point, it is convenient to carry out the ampho-ionization reaction with respect to the formed product of the copolymerization reaction, that is, the copolymer solution.

The halogens of sodium or potassium haloacetate, which are ampho-ionization agents, are chlorine, bromine, and iodine, of which chlorine is representative. This s a l t can also be formed in situ by causing haloacetic acid and sodium hydroxide or potassium hydroxide to react in the ampho-ionization reaction solvent.

The ampho-ionization reaction can be carried out by adding, either in one lot or in divisional lots, the sodium or potassium haloacetate as it is or in the form of a solution or a suspension to the copolymer solution (preferably of a copolymer concentration of the order of 30 to 65 percent) and heating these materials at a temperature of 70° to 80° C. for a reaction time of the order of 4 to 8 hours in an inactive atmosphere, for example, a stream of nitrogen gas, with suitable agitation.

The quantity in which the sodium or potassium haloacetate is used is ordinarily of the order of 70 to 130 percent, preferably 80 to 120 percent of the stoichiometric quantity, that is, equimolar quantity relative to the monomer (1) (and the monomer (5) in the case where it contains the nitrogen atom to be ampho-ionized).

4. Separation

When the solvent for the ampho-ionization reaction has been appropriately selected, a by-product inorganic salt, that is, a sodium or potassium halide, precipitates (although it does not necessarily settle as a sediment) in the copolymer solution after the ampho-ionization and thus separates. Accordingly, this precipitate is removed.

The removal of the precipitate may be carried out by centrifuging, filtering, or any other suitable method of separating solids from liquids.

By removing the solvent after the precipitation (or after the ion-exchange resin treatment described hereinafter), the resin of this invention can be obtained as a solid.

5. Ion-exchange resin treatment

A small quantity (of the order of 0.1 to 1 percent) of the by-product inorganic salt is still contained in some instances in the ampho-ionization copolymer solution from which the precipitate has been separated in the above described manner.

When it is desired to fully remove even this inorganic salt, the ampho-ionization copolymer solution after precipitation and separation is treated with an ion-exchange resin by a batch process or a flow precess, whereby the ash content can be reduced to 0.1 percent or less.

6. Form of hairdressing

A resin of this invention obtained in this manner can be used as it is in the case where it has been obtained as a solution. Alternatively, the resin can be used as a hairdressing agent or a resin component of a hairdressing agent after removal of the solvent.

The preferred mode of use of the resin of this invention is the use thereof in the form of an aerosol comprising a solution of the resin and a propellant which have been pressurized and sealed together in a container and sprayed for application to hair.

The application of a resin for hairdressing in the form of an aerosol to hair is known. A resin of this invention also can be similarly sealed in an aerosol dispenser and used. Accordingly, the resin is dissolved in the solvent for the ampho-ionized copolymer, preferably a hydrophilic solvent (as defined hereinbefore) and, together with an aerosol propellant and suitable additive(s) and/or adjuvant(s), is pressurized and sealed in a conventional aerosol dispenser.

Examples of the hydrophilic solvent are, as the solvent for polymerization, aliphatic alcohols as described hereinbefore, ethers such as dioxane, ketones such as methylethyl ketones, acetone, and ether alcohols such as methyl Cellosolve, ethyl Cellosolve, etc. A conventional aerosol propellant such as fluoro- or fluorochloroalkanes (known as "Freons"), other hydrocarbon halides, hydrocarbons such as butane gas, or other liquefied petroleum gases can be used. The additive and/or adjuvant added in this case may be charged substance since the resin of this invention is ampho-ionic. For example, plasticizers such as higher alcohol esters of higher fatty acids, glycerol, and polyethylene glycol, suitable perfumes, lustering agents, coloring agents, nutritive agents for hair and scalp, and other substances can be added without giving rise to deterioration of the additive(s) or of the resin itself. One example of a hair spray composition of general type in which the resin of this invention is used is set forth below.

| Ingredient | Percent |
|---|---|
| Propellant ("Freon") | 60 approx. |
| Resin | 2 to 10 |
| Ethanol | 37 to 34 |
| Lustering agent (PEG compound) | 1 approx. |
| Perfume, etc. | some |

In addition, and ampho-ionic resin of this invention can be used also in so-called setting lotions, hair lotions, hair liquids, shampoos, rinses, hair creams, and other hair preparations. The term "for hairdressing" is herein used to designate such uses of the resins of this invention.

7. Examples of experiments

EXAMPLE 1

In a five-necked flask provided with a reflux condenser, a dropping funnel, a thermometer, a glass tube for atmospheric replacement with nitrogen, and an agitating device were placed 30 parts of dimethylaminoethyl methacrylate, 30 parts of methyl methacrylate, 15 parts of 2-ethylhexyl methacrylate, 15 parts of dodecyl methacrylate, 10 parts of N-vinyl pyrrolidone, and 100 parts of anhydrous ethanol. 0.6 part of $\alpha,\alpha'$-azobisisobutyronitrile was then added, and polymerization was carried out for 4 hours by reflux heating at 80° C. in a stream of nitrogen gas.

Next, a 50-percent ethanol suspension of potassium monochloroacetate in a quantity equimolar to the dimethylaminoethyl methacrylate in the copolymer was dropped into the flask through the dropping funnel, and ampho-ionization reaction was carried out by further heating at 80° C. for 6 hours in a nitrogen gas stream, whereupon a viscous suspension was obtained.

A precipitate was separated from this suspension by means of a pressurizing filter (manufactured by Nippon Senshoku Kikai K.K., Japan).

The filtrate was passed through a column packed with a regenerated cation-exchange resin ("Daiya-ion PK-220," which had been prepared by substitution of the system with anhydrous ethanol after regeneration) and was then passed through a column packed with a regenerated anion-exchange resin ("Daiya-ion PA-416,") which had been prepared by substitution of the system with anhydrous ethanol after regeneration). As a result, a light yellow, transparent solution was obtained.

This solution was adjusted to an active ingredient concentration of 30 percent with anhydrous ethanol. To 6 parts of this solution, 24 parts of anhydrous ethanol was added to dissolve the solution. Then 45 parts of dichlorodifluoromethane was added to the resulting solution. The solution thus obtained was charged into a sealed container to be sprayed therefrom and used as a hair lacquer.

When this hair lacquer was sprayed onto hair it exhibited good setting strength with a natural feel without the occurrence of blocking and flaking. This hair lacquer also had compatibility with the propellant used and excellent film properties. Furthermore, when this solution was left in a tin can at 45° C. for 6 months, no corrosion of the inner surface of the can was observable after that period.

EXAMPLES 2 THROUGH 6 (REF., TABLE 1)

Except for initial monomer compositions as set forth in Table 1, the procedure of Example 1 was followed to obtain five resin solutions. Similarly as in the case of the resin solution obtained in Example 1, these five resin solutions of Examples 2 through 6 exhibited good setting strength, compatibility with the propellant, and excellent film properties without blocking or flaking.

COMPARISON EXAMPLES 1 THROUGH 8 (REF., TABLE 2)

Except for initial monomer compositions as set forth in Table 2, the procedure of Example 1 was followed to obtain eight resin solutions. When these resin solutions were examined, they were found to be defective in at least one item among the items of performance as setting agents relating to compatibility with a propellant, ease of being removed by washing, blocking, smoothness, and transparency and other film properties. Furthermore, the resin sample of Comparison Example 8 was found to be deficient in setting strength.

The evaluations of the various items of performance as indicated in Tables 1 and 2 were made in the following manner. In the tables, the symbol o indicates "good", Δ indicates "insufficient," and x indicates "defective."

(1) Compatibility with propellant

In a pressurized container, 60 parts of Freon gas of a ratio $F_{11}/F_{12}$ of 20/30 (weight ratio) was charged into 40 parts of an alcohol solution containing 5 percent (dry basis) of the resin being tested. The temperature of the resulting solution was progressively decreased, and the temperature at which a polymer precipitated was measured.

(2) Film properties

The solution to be tested was sprayed onto a glass plate and left for 24 hours in an atmosphere at a temperature of 20° C. and a relative humidity of 60 percent. The resulting film was then evaluated by visible appearance and tactile feel.

The ease with which the resin can be removed by washing was evaluated by gently immersing the above mentioned glass plate with the resin film in warm water at 40° C. containing 0.2 percent of a shampoo and observing the dissolving state of the film every hour.

(3) Setting strength

The solution to be tested was sprayed for 10 seconds onto a lock of hair of 23-cm. length and 2-gram weight, which was then wound around a curler of 1.2-cm. diameter. After the solution had dried, the lock of hair was suspended in an atmosphere at 30° C. and 90-percent RH, and the curl retention was measured.

(4) Flaking

A lock of hair prepared in the same manner as described above for the setting strength evaluation was combed with a comb, and the quantity of resin peeled off was evaluated.

TABLE 1

| | | | | | | | | | | | Performance | | | | | |
| | | | | | | | | | | Com- | | Film properties | | | | |
| | | | | | | | | | | pati-bility with pro- | Re-mov-abili-ty by | | | | | |
| Example | Monomer (1) | | Monomer (2) | | Monomer (3) | | Monomer (4) or Monomer (5) | | | pellant (°C.) | wash-ing (min) | Block-ing | Smooth-ness | Trans-par-ency | Flak-ing | Set-ting strength |
|---|---|---|---|---|---|---|---|---|---|---|---|---|---|---|---|---|
| 1 | dimethyl-amino-ethyl meth-acrylate | 30 | methyl meth-acry-late | 30 | 2-ethylhe-xyl meth-acrylate tridecyl meth-acrylate | 15 15 | N—vinyl pyrroli-done | 10 | | o (<−50) | o (40) | o | o | o | o | o |
| 2 | dimethyl-amino-ethyl meth-acrylate | 30 | iso-propyl meth-acry-late | 45 | stearyl methacry-late | 20 | N—vinyl pyrroli-done | 15 | | o (<−50) | o (15) | o | o | o | o | o |
| 3 | diethyl-amino-ethyl meth-acrylate | 30 | methyl meth-acry-late | 20 | cyclohexyl meth-acrylate tridecyl meth-acrylate | 16 17 | N—vinyl pyrroli-done diacetone acrylamide | 10 7 | | o (<−50) | o (20) | o | o | o | o | o |
| 4 | dimethyl-amino-ethyl meth-acrylate | 40 | ethyl meth-acry-late | 10 | lauryl meth-acrylate tridecyl meth-acrylate | 20 20 | vinyl acetate | 10 | | o (<−50) | o (10) | o | o | o | o | o |
| 5 | dimethyl-amino-ethyl meth-acrylate | 40 | ethyl acry-late | 10 | lauryl meth-acrylate tridecyl meth-acrylate | 30 20 | | | | o (<−50) | o (30) | o | o | o | o | o |
| 6 | dimethyl-amino-ethyl meth-acryl- | 40 | | | isobutyl meth-acrylate lauryl meth- | 30 30 | | | | o (<−50) | o (30) | o | o | o | o | o |

TABLE 1-continued

| Example | Monomer composition (% by weight) | | | | Compatibility with propellant (°C.) | Removability by washing (min) | Blocking | Smoothness | Transparency | Flaking | Setting strength |
|---|---|---|---|---|---|---|---|---|---|---|---|
| | Monomer (1) | Monomer (2) | Monomer (3) | Monomer (4) or Monomer (5) | | | | | | | |
| | amide | | acrylate | | | | | | | | |

TABLE 2

| Comparison Example | Monomer composition (% by weight) | | | | Compatibility with propellant (°C.) | Removability by washing (min) | Blocking | Smoothness | Transparency |
|---|---|---|---|---|---|---|---|---|---|
| | Monomer (1) | Monomer (2) | Monomer (3) | Monomer (4) or Monomer (5) | | | | | |
| 1 | dimethylaminoethyl methacrylate 10 | butyl acrylate 50 | lauryl methacrylate 40 | | O (<−50) | X (60) | X | Δ | O |
| 2 | dimethylaminoethyl methacrylate 20 | methyl methacrylate 35 | tridecyl methacrylate 2; lauryl methacrylate 15 | N—vinyl pyrrolidone 10 | O (<−50) | Δ (60) | O | O | O |
| 3 | dimethylaminoethyl methacrylate 30 | methyl methacrylate 60 | lauryl methacrylate 10 | | Δ (20<) | Δ (60) | O | O | O |
| 4 | dimethylaminoethyl methacrylate 30 | methyl methacrylate 2 | stearyl methacrylate 68 | | O (<−50) | Δ (60) | Δ-O | Δ | Δ |
| 5 | dimethylaminoethyl methacrylate 30 | methyl methacrylate 68 | lauryl methacrylate 2 | | Δ (20<) | Δ (60) | O | O | O |
| 6 | dimethylaminoethyl methacrylate 30 | methyl methacrylate 0 | stearyl methacrylate 70 | | O (<−50) | Δ (60) | Δ-O | Δ | Δ |
| 7 | dimethylaminoethyl methacrylate 30 | methyl methacrylate 48 | lauryl methacrylate 2 | N—vinyl pyrrolidone 20 | Δ (20<) | O (1) | Δ-O | O | O |
| 8 | dimethylaminoethyl methacrylate 50 | methyl methacrylate 30 | lauryl methacrylate 20 | | O (−10) | O (1) | Δ-O | O | O |

What we claim is:

1. A resin for hairdressing obtained by a process which comprises:

copolymerizing, in a hydrophilic solvent, monomers of a monomer composition comprising:

25 to 45 percent by weight of a first monomer (1) represented by the formula

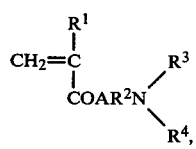

0 to 50 percent by weight of a second monomer (2) represented by the formula

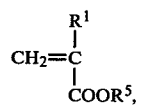

5 to 65 percent by weight of a third monomer (3) represented by the formula

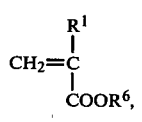

0 to 20 percent by weight of a fourth monomer (4) which is a hydrophilic ethylenically unsaturated monomer, and 0 to 20 percent by weight of a fifth monomer (5) which is an ethylenically unsaturated monomer other than the monomers (1) through (4), the total content of the monomer (1) unit and the monomer (4) unit being 35 percent by weight at the least, in which formulas: $R^1$ is a hydrogen atom or a methyl radical; $R^2$ is an alkylene radical having 1 to 4 carbon atoms; each of $R^3$ and $R^4$ is a hydrogen atom or an alkyl radical having 1 to 4 carbon atoms; $R^5$ is an alkyl or alkenyl radical having 1 to 3 carbon atoms; $R^6$ is an alkyl or alkenyl radical having 4 to 24 carbon atoms or a cycloalkyl radical having 4 to 24 carbon atoms; and A is oxygen (O) or NH;

causing the copolymer thus formed to react in the state of a solution in a hydrophilic solvent with sodium or potassium monochloroacetate;

removing any precipitate formed as by-product; and, subjecting the copolymer solution thus obtained to an ion-exchange resin treatment thereby to remove ionic impurities.

2. A process for producing a resin for hairdressing which comprises:

copolymerizing, in a hydrophilic solvent, monomers of a monomer composition comprising:

25 to 45 percent by weight of a first monomer (1) represented by the formula

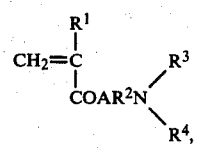

0 to 50 percent by weight of a second monomer (2) represented by the formula

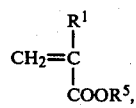

5 to 65 percent by weight of a third monomer (3) represented by the formula

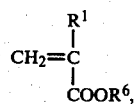

0 to 20 percent by weight of a fourth monomer (4) which is a hydrophilic ethylenically unsaturated monomer, and 0 to 20 percent by weight of a fifth monomer (5) which is an ethylenically unsaturated monomer other than the monomers (1) through (4), the total content of the monomer (1) unit and the monomer (4) unit being 35 percent by weight at the least, in which formulas: $R^1$ is a hydrogen atom or a methyl radical; $R^2$ is an alkylene radical having 1 to 4 carbon atoms; each of $R^3$ and $R^4$ is a hydrogen atom or an alkyl radical having 1 to 4 carbon atoms; $R^5$ is an alkyl or alkenyl radical having 1 to 3 carbon atoms; $R^6$ is an alkyl or alkenyl radical having 4 to 24 carbon atoms or a cycloalkyl radical having 4 to 24 carbon atoms; and A is oxygen (O) or NH;

causing the copolymer thus formed to react in the state of a solution in a hydrophilic solvent with sodium or potassium monochloroacetate;

removing any precipitate formed as by-product; and, subjecting the copolymer solution thus obtained to an ion-exchange resin treatment thereby to remove ionic impurities.

3. A resin according to claim 1 in which said first monomer is selected from a member of the group consisting of dimethylaminoethyl methacrylate, diethylaminoethyl methacrylate, and diethylaminoethyl methacrylamide.

4. A resin according to claim 1 in which said second monomer is selected from the group consisting of methyl methacrylate, ethyl methacrylate, isopropyl methacrylate and ethyl acrylate.

5. A resin according to claim 1, 3 or 4 in which said third monomer is selected from at least one member of the group consisting of 2-ethylhexyl methacrylate, tridecyl methacrylate stearyl methacrylate, cyclohexyl methacrylate, lauryl methacrylate and isobutyl methacrylate.

6. A resin according to claim 1, 3 or 4 in which said fourth monomer is selected from a member of the goup consisting of N-vinylpyrrolidone, acrylamide, hydroxyethyl acrylate, hydroxyethyl methacrylate, hydroxypropyl acrylate, hydroxypropyl methacrylate, polyethyleneglycol monoacrylate, polyethyleneglycol monomethacrylate, polypropyleneglycol monomethacrylate, and polypropyleneglycol monoacrylate.

7. A resin according to claim 1, 3 or 4 in which said fifth monomer is selected from a member of the group consisting of acrylonitrile, styrene, chlorostyrene, vinyltoluene, vinyl acetate, polypropyleneglycol monoacrylate, polypropyleneglycol monomethacrylate, vinyltrichlorosilane, methacryloxypropyl trimethoxy silane and diacetone acrylamide.

8. A resin according to claim 1 in which the quantity of the first monomer is about 30 to 40 percent by weight, the quantity of the second monomer is about 5 to 40 percent by weight, the quantity of the third monomer is about 10 to 50 percent by weight, the quantity of the fourth monomer is about 0 to 15 percent by weight and the quantity of the fifth monomer is about 0 to 10 percent by weight.

9. A process according to claim 2 in which said first monomer is selected from a member of the group consisting of dimethylaminoethyl methacrylate, diethylaminoethyl methacrylate and diethylaminoethyl methacrylamide.

10. A process according to claim 2 in which said second monomer is selected from the group consisting of methyl methacrylate, ethyl methacrylate isopropyl methacrylate and ethyl acrylate.

11. A process according to claim 2, 9 or 10 in which said third monomer is selected from at least one member of the group consisting of 2-ethylhexyl methacrylate, tridecyl methacrylate, stearyl methacrylate, cyclohexyl methacrylate, lauryl methacrylate and isobutyl methacrylate.

12. A process according to claim 2, 9 or 10 in which said fourth monomer is selected from a member of the group consisting of N-vinylpyrrolidone, acrylamide, hydroxyethyl acrylate, hydroxyethyl methacrylate, hydroxypropyl acrylate, hydroxypropyl methacrylate, polyethyleneglycol monoacrylate, polyethyleneglycol monomethacrylate, polypropyleneglycol monoacrylate and polypropyleneglycol monomethacrylate.

13. A process according to claim 2, 9 or 10 in which said fifth monomer is selected from a member of the group consisting of acrylonitrile, styrene, chlorostyrene, vinyltoluene, vinyl acetate, polypropyleneglycol monoacrylate, polypropyleneglycol monomethacrylate, vinyltrichlorosilane, methacryloxypropyl trimethoxy silane and diacetone acrylamide.

14. A process according to claim 2 in which the quantity of the first monomer is about 30 to 40 percent by weight, the quantity of the second monomer is about 5 to 40 percent by weight, the quantity of the third monomer is about 10 to 50 percent by weight, the quantity of the fourth monomer is about 0 to 15 percent by weight and the quantity of the fifth monomer is about 0 to 10 percent by weight.

* * * * *